United States Patent
Price

(10) Patent No.: US 10,986,837 B2
(45) Date of Patent: Apr. 27, 2021

(54) LACTAM SOLUBILITY

(71) Applicant: Conopco, Inc., Englewood Cliffs, NJ (US)

(72) Inventor: Paul Damien Price, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/750,912

(22) PCT Filed: Aug. 10, 2016

(86) PCT No.: PCT/EP2016/069072
§ 371 (c)(1),
(2) Date: Feb. 7, 2018

(87) PCT Pub. No.: WO2017/029175
PCT Pub. Date: Feb. 23, 2017

(65) Prior Publication Data
US 2018/0228154 A1 Aug. 16, 2018

(30) Foreign Application Priority Data
Aug. 20, 2015 (EP) .................................... 15181851

(51) Int. Cl.
| | |
|---|---|
| A01N 43/36 | (2006.01) |
| A01N 25/30 | (2006.01) |
| A61K 8/49 | (2006.01) |
| A61Q 17/00 | (2006.01) |

(52) U.S. Cl.
CPC ............ *A01N 43/36* (2013.01); *A01N 25/30* (2013.01); *A61K 8/4913* (2013.01); *A61Q 17/005* (2013.01)

(58) Field of Classification Search
CPC combination set(s) only.
See application file for complete search history.

(56) References Cited

U.S. PATENT DOCUMENTS

| | | | |
|---|---|---|---|
| 5,955,419 A | 9/1999 | Barket, Jr. et al. | |
| 7,985,722 B2* | 7/2011 | DeSanto | A01N 63/10 510/160 |
| 8,641,948 B2 | 2/2014 | Ghogh et al. | |
| 9,586,901 B2 | 3/2017 | Kumar et al. | |
| 9,930,888 B2 | 4/2018 | Parry et al. | |
| 10,306,886 B2 | 6/2019 | Price | |
| 2007/0269473 A1 | 11/2007 | Nelson | |
| 2009/0175810 A1 | 7/2009 | Winckle | |
| 2011/0059144 A1 | 3/2011 | Fletcher | |
| 2011/0257115 A1* | 10/2011 | Leighton | A61K 45/06 514/25 |
| 2012/0190667 A1 | 7/2012 | Ghogh et al. | |
| 2013/0142855 A1* | 6/2013 | Gross | A01N 43/16 424/408 |
| 2013/0190377 A1 | 7/2013 | Kumar et al. | |
| 2013/0330292 A1 | 12/2013 | Lei et al. | |
| 2014/0017287 A1 | 1/2014 | Lei et al. | |
| 2014/0294925 A1* | 10/2014 | Yin | A61K 31/7028 424/450 |
| 2014/0296336 A1 | 10/2014 | Berndl et al. | |
| 2015/0073069 A1 | 3/2015 | De Gans et al. | |
| 2015/0351393 A1 | 12/2015 | Parry et al. | |

FOREIGN PATENT DOCUMENTS

| | | | |
|---|---|---|---|
| CN | 1169112 | 12/1997 | |
| CN | 1688543 | 10/2005 | |
| CN | 101410372 | 4/2009 | |
| CN | 101932300 | 12/2010 | |
| CN | 102257117 | 11/2011 | |
| CN | 103260609 | 8/2013 | |
| WO | WO2004016588 | 2/2004 | |
| WO | WO2006085089 | 8/2006 | |
| WO | WO2007085042 | 8/2007 | |
| WO | WO2010069742 | 6/2010 | |
| WO | WO2012156250 | 11/2012 | |
| WO | WO2014118240 | 8/2014 | |
| WO | WO-2014118240 A1 * | 8/2014 | ............... A61Q 5/12 |
| WO | WO2017029112 | 2/2017 | |

OTHER PUBLICATIONS

Search Report and Written Opinion in PCTEP2016067616, dated Sep. 12, 2016.
Search Report and Written Opinion in PCTEP2016068008, dated Sep. 12, 2016.
Search Report and Written Opinion in PCTEP2016068010, dated Sep. 12, 2016.
Search Report and Written Opinion in PCTEP2016068287, dated Oct. 26, 2016.
Search Report and Written Opinion in PCTEP2016068585, dated Oct. 4, 2016.
Search Report and Written Opinion in PCTEP2016068625, dated Sep. 9, 2016.
Search Report in EP15181842, dated Dec. 10, 2015.
Search Report in EP15181846, dated Dec. 11, 2015.
Search Report in EP15181847, dated Dec. 17, 2015.
Search Report in EP15181851, dated Dec. 11, 2015.
Search Report in EP15181856, dated Dec. 14, 2015.
Wei et al.; Measurement and Correlation of the Solubility of Penicillin V Potassium in Ethanol + Water and 1-Butyl Alcohol + Water Systems; Journal of Chemical and Engineering Data; 2015; 112-117; vol. 60, No. 1.
Kerwin et al.; Polysorbate 20 and 80 Used in the Formulation of Protein Biotherapeutics: Structure and Degradation Pathways; Journal of Pharmaceutical Sciences; Aug. 2008; pp. 2924-2937; vol. 97; Wiley InterScience.
Borate et al.; Novel hybrids of fluconazole and furanones: Design, synthesis and antifungal activity; Bioorganic & Medicinal Chemistry Letters; 2011; pp. 4873-4878; vol. 21.
Munoz, et al.; Enzymatic enantiomeric resolution of phenylethylamines; Org. Biomol. Chem.; 2011; pp. 8171-8177 (abstract only—total 5 pages); vol. 9.

(Continued)

*Primary Examiner* — Jared Barsky
(74) *Attorney, Agent, or Firm* — Foley & Lardner LLP

(57) ABSTRACT

Compositions comprising lactams and biosurfactants, suitable for use as antimicrobial, anti-biofilm and bacteriostatic compositions.

18 Claims, No Drawings

(56) References Cited

OTHER PUBLICATIONS

Luo Mingsheng, Gao Tianhu; Overview of Pharmaceutical Excipients; Overview of Pharmaceutical Excipients; 2006; pp. 627-628 (translation of relevant portions only).
Subbarao et al; Functions of Hydrotropes in Solutions; Chemical Engineering Technology; 2012; 225-237; 35(2).
Lin Hui, et al.; Micellization properties of different rhamnolipidic fractions and their solubilization; Acta Scientiae Circumstantiae; 2011; 2609-2615 (with Engl. Abstract and human translation of pp. 2610 & 2614 only); 31, No. 12.
Kloeppel; Temperature inside collapsing bubble four times that of sun; News Bureau—Research, ; 2005; pp. 1-3.
IPRP in PCTEP2016069072, Aug. 2, 2017.
IPRP2 in PCTEP2016068585, Nov. 2, 2017.
IPRP2 in PCTEP2016068625, Sep. 6, 2017.
Search Report & Written Opinion in EP15181849, dated Feb. 23, 2016.
Search Report & Written Opinion in PCTEP2016069072, dated Sep. 14, 2016.
Search Report and Written Opinion in PCTEP2016067613, dated Sep. 21, 2016.
Search Report in EP15181858, dated Dec. 11, 2015.
Written Opinin in EP15181856, dated Dec. 14, 2015.
Written Opinion 2 in PCTEP2018067613, dated Jul. 11, 2017.
Written Opinion in EP15181842, dated Dec. 10, 2015.
Written Opinion in EP15181846, dated Dec. 11, 2015.
Written Opinion in EP15181847, dated Dec. 17, 2015.
Written Opinion in EP15181851, dated Dec. 11, 2015.
Written Opinion in EP15181858, dated Dec. 11, 2015.
Ondrej Krenk et al., Methodology for Synthesis of Enantiopure 3,5-Disubstituted Pyrrol-2-ones, European Journal of Organic Chemistry, 2015, pp. 5414-5423; XP002752111.
Marye. Davey et al., Rhamnolipid Surfactant production Affects Biofilm Architecture in Pseudomonas aeruginosa PAO1, Journal of Bacteriology, 2003, pp. 1027-1036, vol. 185, No. 3, American Society for Microbiology.

\* cited by examiner

LACTAM SOLUBILITY

This application claims priority from EP 15181851.5 filed 20 Aug. 2015 which is herein incorporated by reference for all purposes.

The present invention relates to compositions comprising lactams and biosurfactants. The compositions are suitable for use as, for example, antimicrobial, anti-biofilm and bacteriostatic compositions.

WO 2007/085042 and WO 2004/016588 disclose lactams for antimicrobial benefit and steps towards their synthesis. WO2014/118240 discloses antimicrobial compositions comprising a lactam and a hydrotope.

However, use of these lactams is limited by compatibility with certain formulations and, in particular, solubility in certain aqueous solutions.

The present invention relates to compositions comprising lactams and biosurfactants. The inventor(s) have found that, surprisingly, the presence of a non-ionic surfactant advantageously improves lactam solubility.

More specifically, the present invention relates to compositions comprising lactams as described in WO 2007/085042 and WO 2004/016588, the contents of which, and in particular the lactam structures explicitly drawn out therein, are incorporated by reference. The compositions further comprise a lactam and a biological surfactant.

For example, in a first aspect, the present invention relates to a compositions comprising a lactam and a biological surfactant, wherein the lactam is a lactam of formula (I) or (II):

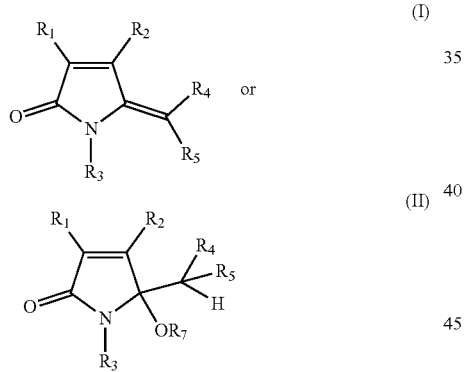

wherein:
$R_1$ and $R_2$ are each independently selected from hydrogen, halogen, alkyl, cycloalkyl, alkoxy, oxoalkyl, alkenyl, heterocyclyl, heteroaryl, aryl and aralalkyl; and
$R_3$ is selected from hydrogen, hydroxyl, alkyl, cycloalkyl, alkoxy, oxoalkyl, alkenyl, heterocyclyl, heteroaryl, cycloalkyl, aryl, aralalkyl and —C(O)CR$_6$=CH2;
$R_4$ and $R_5$ are independently selected from hydrogen, aryl, heterocyclyl, heteroaryl, and arylalkyl; and
$R_6$ is selected from hydrogen and methyl; and
$R_7$ is selected from hydrogen and —C(O)CR$_6$=CH$_2$; and
Preferably, at least one of $R_4$ and $R_5$ is hydrogen.

It will be appreciated that, where appropriate groups may be optionally substituted. Optional substituents may include halogens, $C_{1-4}$alkyl, $C_{1-4}$haloalkyl (for example, CF$_3$) and $C_{1-4}$alkoxy.

Alkyls may, for example, be $C_{1-12}$alkyls, such as $C_{1-6}$alkyls. Aryls may, for example, be $C_{6-10}$aryls, for example, phenyls.

Preferably, at least one of $R_1$ and $R_2$ is selected from heterocyclyl, heteroaryl, aryl and arylalkyl.

Preferably, $R_1$ is hydrogen. Preferably, $R_3$ is hydrogen. Preferably, $R_4$ is hydrogen. Preferably, $R_5$ is hydrogen. Preferably, $R_6$ is hydrogen. Preferably, $R_7$ is hydrogen. Preferably, $R_2$ is aryl or aralalkyl. More preferably, $R_2$ is a phenyl group or a substituted phenyl group, for example, a mono-substituted phenyl group. Substitution may be ortho, meta, or para. Preferably, it is para. Preferred substituents include halogen and methyl. For example, and without limitation, $R_2$ may be selected from phenyl, 4-fluorophenyl, 4-chlorophenyl, 4-bromophenyl and 4-methylphenyl.

Accordingly, in a first aspect, the present invention may provide a composition comprising a lactam and a biosurfactant, wherein the lactam is a lactam of Formula Ia or Formula IIa:

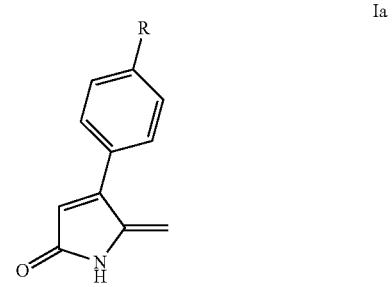

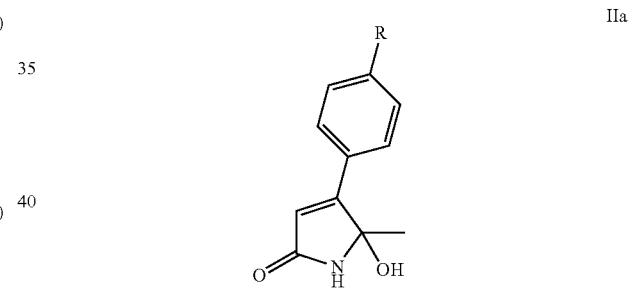

wherein R is H, halogen (preferably, F, Cl, or Br), or $C_{1-4}$alkyl (preferably methyl).

In some embodiments, the lactam is a lactam of formula Ia. In some embodiments, the lactam is a lactam of formula IIa.

Preferred lactams may include:

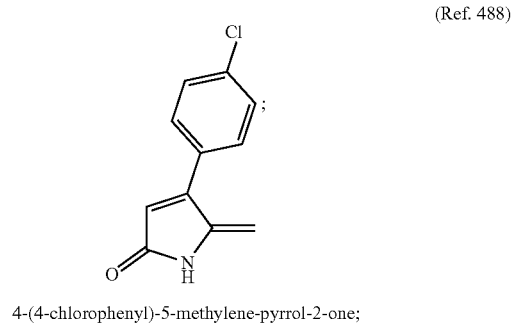

4-(4-chlorophenyl)-5-methylene-pyrrol-2-one;

-continued (Ref. 491)

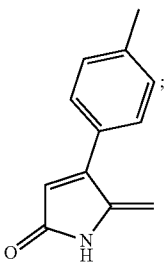

5-methylene-4-(p-tolyl)pyrrol-2-one (Ref. 131)

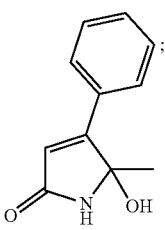

4-phenyl-5-hydroxy-5-methyl-1H-pyrrol-2-one (Ref. 258)

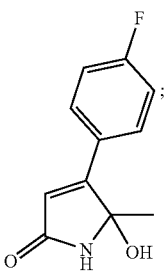

4-(4-fluorophenyl)-5-hydroxy-5-methyl-1H-pyrrol-2-one (Ref. 316)

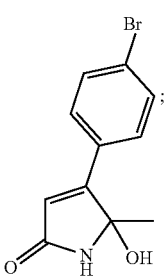

4-(4-bromophenyl)-5-hydroxy-5-methyl-1H-pyrrol-2-one.

The composition may be, without limitation, any homecare composition (institutional, organizational or consumer home) or a personal care composition such as a skin cream or a serum, or an industrial composition such as an anti-biofilm coating or paint, for example, for use in maritime environments. The composition may also be an agricultural chemical. The compositions may be suitable for use as antimicrobial compositions. The compositions may also be used as additive compositions; in other words, the composition may be combined with further ingredients such as excipients to form a composition as described above.

Suitably, the composition is an aqueous composition. It may be a non-aqueous composition.

Preferably the composition contains 0.000001 to 50% wt. lactam, more preferably 0.001 to 50% wt. even more preferably 0.01 to 5% wt, most preferably 0.01 to 2%.

The biosurfactant preferably comprises a microbially-derived biosurfactant. Preferably it comprises a glycolipid biosurfactant moiety which may be a rhamnolipid or sophorolipid or trehalolipid or a mannosylerythritol lipid (MEL) or combinations thereof.

Alternatively or additionally the biosurfactant may comprise any shear thinning biosurfactant and in this respect, may extend to include any shear thinning glycolipid biosurfactant mentioned above or any shear thinning cellobiose, peptide based biosurfactant, lipoprotein, lipopeptide e.g. surfactin, fatty acids e.g. corynomucolic acids (preferably with hydrocarbon chain C12-C14), phospholipid (e.g.

Phosphatidylethanolamine produced by *Rhodococcus erythropolis* grown on n-alkane resulted in the lowering of interfacial tension between water and hexadecane to less than 1 mN m$^{-1}$ and CMC of 30 mg L$^{-1}$ (Kretschner et al., 1982)), spiculisporic acid, polymeric biosurfactants including emulsan, liposan, mannoprotein or polysaccharide-protein complexes or combinations thereof.

Preferably, the biosurfactant is a rhamnolipid or a sophorolipid.

Preferably the biosurfactant moiety comprises a rhamnolipid.

The biosurfactant moiety may comprise one or more saccharide moieties such as sugar rings. In the case of rhamnolipids the rhamnolipid may comprise one or both components: mono-rhamnolipids having a single rhamnose sugar ring and di-rhamnolipids, having two rhamnose sugar rings.

In the case of rhamnolipids, throughout this patent specification, the prefixes mono- and di- are used to indicate respectively to indicate mono-rhamnolipids (having a single rhamnose sugar ring) and di-rhamnolipids (having two rhamnose sugar rings) respectively. If abbreviations are used R1 is mono-rhamnolipid and R2 is di-rhamnolipid.

Sophorolipids comprise a hydrophobic fatty acid tail and a hydrophilic carbohydrate sophotose head. The fatty acid tail may be saturated or unsaturated. Sophorolipids are known in the art.

The ratio of lactam to biosurfactant surfactant may, for example, be from 1:0.5 to 1:20, preferably from 1:0.5 to 1:10, such as from 1:0.5 to 1:5.

The biosurfactant can be used to replace at least 50 wt. % of a total surfactant in the composition.

Preferably the biosurfactant is present at a level of 20-90 wt. % of the total surfactant and more preferably the biosurfactant is present at 50-80 wt. % of the total surfactant and more preferably 50-75% wt. % of the total surfactant.

The composition may be, without limitation, any of a personal care composition, a homecare composition, a pharmaceutical composition, or an industrial composition such as an anti-biofilm coating or paint, for example, for use in maritime environments. The composition may also be an agricultural chemical. The compositions may be suitable for use as antimicrobial, anti-biofilm and bacteriostatic compositions. Non-limiting examples of such compositions are provided herein. The compositions may also be used as additive compositions; in other words, the composition may be combined with further ingredients such as excipients to form a composition as described above.

DESCRIPTION

Lactams may be obtained using methods as described in WO 2007/085042 and WO 2004/016588, which are herein incorporated by reference in their entirety.

Compositions

The compositions described herein may be compositions having anti-microbial activity. In some cases, the compositions are anti-bacterial. They may have bactericidal and/or bacteriostatic activity. The inventor(s) have observed desirable bacteriostatic activity. Accordingly, in some cases, the composition is a bacteriostatic composition.

The compositions may also prevent and/or inhibit biofilm formation. Biofilms are formed when microorganisms stick to a surface. Biofilm extracellular polymeric substances may be formed. Biofilms (also referred to as slime) present problems in industrial environments; for example, they may form in pipes in apparatus, or industrial and agricultural structures, on solar panels, and on boat hulls and other marine structures. Biofilms may also pose a problem in domestic environments. For example, biofilms may form in domestic appliances such as washing machines. Biofilms are also present in personal care, for example, they may form on tooth surfaces.

Compositions suitable for any and all of these applications are within the scope of the invention. In some cases, the composition is a paint or other coating. In such cases, the composition may further comprise a binder, optionally a pigment and optionally one or more conventional additives (for example, to modify surface tension, improve flow properties, improve the finished appearance, increase wet edge, improve pigment stability, etc—such additives are known in the art). The composition may comprise an aqueous solvent or an organic solvent to suit purpose.

The composition may also be used in medical applications, for example to coat equipment including medical devices.

In some cases, the composition is a pharmaceutical composition. In other words, the composition may comprise a lactam as described herein and a pharmaceutically acceptable excipient. The composition may be suitable for topical use (for example, it may be a cream or lotion), it may be suitable for ocular use (for example, it may be an used as a pharmaceutical eye drop), it may be suitable for otic use (for example, it may be used as an ear drop), it may be suitable as a mouth wash, or it may be suitable for oral administration.

In some cases, the composition is a composition suitable for use in the home (often referred to as a homecare composition) or institutions. Homecare compositions include, without limitation, cleaning products, laundry detergents, and fabric conditioners. In some cases, the composition is a homecare composition, for example a laundry liquid. The composition may therefore comprise a detergent surfactant and a builder. The composition may be a fabric conditioner (also called a fabric softener) and may comprise an antistatic agent. The composition may also be a domestic cleaning product.

In some cases, the composition is a personal care composition. For example, the composition may be intended for use on the skin (for example, a cream, cleanser or serum). For example, the composition may be useful in the prevention or treatment of acne. For example, the composition may comprise one or more of dimethicone, petrolatum, a humectant such as hyaluronic acid or glycerin; and ceramide(s). In some cases, the composition is a personal care composition comprising a detergent, for example, the composition may be a face wash or shower gel or hair shampoo. The composition may be a hair treatment composition other than a shampoo. The composition may be a deodorant composition (for example, a deodorant powder, paste or liquid). The composition may be an oral care composition (such as a toothpaste or mouthwash and may include, for example, fluoride and/or flavourings.

In some cases, the composition is a contact lens cleaning fluid.

The composition may be a composition suitable for use in agriculture, for example, as a soil additive (solid or liquid).

The composition may be a composition suitable for use in the treatment of or manufacture of glass or lens for example as an additive/treatment for solar panels.

Examples

Mono and Di rhamnolipids were extracted and purified from a commercial sample of JBR425, supplied by Jeneil®, using supercritical $CO_2$ using the following method.

A commercial sample of JBR425 (ex Jeneil®) was mixed with a Celllite 454® support and transferred to a supercritical $CO_2$ extractor. The temperature and pressure was increased to produce supercritical $CO_2$ and residual oils and fats were removed from the extractor in a defatting step. A cosolvent, industrial methylated solvent (IMS), was then added to the remaining defatted rhamnolipid mixture on the Cellite 454® support in the presence of supercritical $CO_2$. The co-solvent IMS was introduced at an increasing gradient from 2.5% to 10% to facilitate the separation and removal of the different mono- and di-rhamnolipid ratios.

Bio-surfactant solutions at the levels shown in the results below were prepared for screening. The maximum level tested was dictated by the solubility of the surfactant in water. The following representative example uses 4-(4-chlorophenyl)-5-methylene-pyrrol-2-one.

Solid lactam was weighed into Whatman® Mini Uniprep sample vials, fitted with a 0.45 µm nylon filter (2.7 to 3.3 mg per vial). 50 µL of a solvent solution was placed into each sample vial, the vial capped and shaken briefly by hand to agitate the solid, then placed on a Thermo Labsystems Wellmix® plate shaker and continuously agitated for 48 hours. After this time, the excess solid in the vial was removed using the integral filter membrane and the resultant solution analysed by HPLC to determine the level of dissolved lactam.

Samples were analysed using an Agilent 1200® series HPLC fitted with a Hypersil Gold C18 column (15×2.1×3 µm), using isocratic elution with 60/40 methanol/water (+0.1% Formic Acid) at a flow rate of 0.4 mL/min, using a DAD detector at 285 nm. 4-(4-Chlorophenyl)-5-methylene-pyrrol-2-one has a retention time of ~2.8 minutes.

Each test surfactant solution was tested in triplicate and the mean value of lactam in solution calculated. Values of solubility were quoted as the improvement in aqueous solubility vs water alone (i.e. mean level of lactam dissolved in water+solvent/mean level of lactam dissolved in water) to allow comparison between screens conducted on different days.

| Additive | % Additive in Water | Mean Lactam Level in Solution (ppm) | Solubility Increase vs water alone |
|---|---|---|---|
| Mono-rhamnolipid R1 | 0 | 2.7 | 1.0 |
| | 0.1 | 10.9 | 4.1 |
| | 0.5 | 39.3 | 14.7 |
| | 1 | 75.3 | 28.1 |
| | 2 | 149.7 | 55.9 |
| | 4 | 194.8 | 72.7 |

-continued

| Additive | % Additive in Water | Mean Lactam Level in Solution (ppm) | Solubility Increase vs water alone |
|---|---|---|---|
| Di-rhamnolipid R2 | 0 | 2.7 | 1.0 |
| | 0.1 | 15.2 | 5.7 |
| | 0.5 | 42.6 | 15.9 |
| | 1 | 77.5 | 28.9 |
| | 2 | 139.6 | 52.1 |

The inventor(s) have demonstrated that rhamnolipid biosurfactants are beneficial at increasing lactam solubility in water, in particular at lower concentrations. The best example is R2.

It will be appreciated that, except where expressly provided otherwise, all preferences are combinable.

The invention claimed is:

1. A composition comprising a solution comprising a lactam, at least 0.1% wt. rhamnolipid, and water, wherein the lactam is a lactam of Formula Ia or Formula IIa:

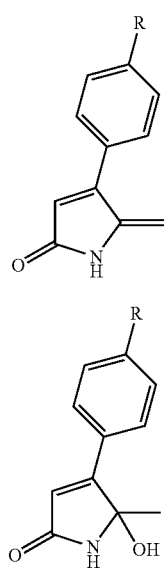

Ia

IIa wherein R is H, halogen, or $C_{1-4}$alkyl wherein the ratio of lactam to rhamnolipid is from 1:0.5 to 1:20.

2. The composition of claim 1, wherein R is H, F, Cl, Br, or Me.

3. The composition of claim 1, wherein the lactam is selected from:

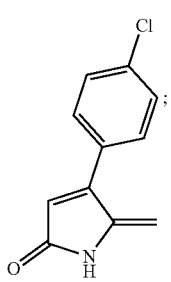

(Ref. 488)

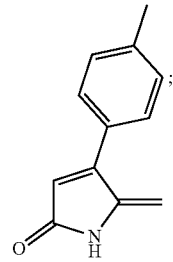

(Ref. 491)

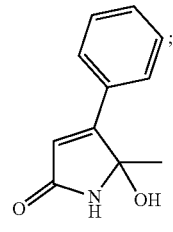

(Ref. 131)

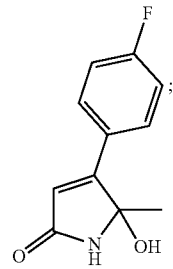

(Ref. 258)

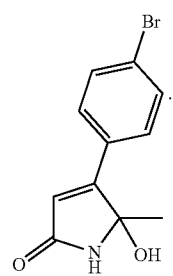

(Ref. 316)

4. The composition of claim 1, wherein the rhamnolipid is a mono-rhamnolipid or a di-rhamnolipid.

5. The composition of claim 1, wherein the composition comprises a surfactant and a glycolipid biosurfactant comprises 20-90% wt. of the total surfactant in the composition.

6. The composition of claim 1, wherein the composition comprises 0.01 to 5% wt. lactam.

7. The composition of claim 1, wherein the lactam is 4-(4-chlorophenyl)-5-methylene-pyrrol-2-one.

8. The composition of claim 1, wherein the composition comprises 0.1% wt. to 4% wt rhamnolipid.

9. A composition comprising a solution comprising lactam, water and at least 0.1% wt. mono-rhamnolipid or di-rhamnolipid, wherein the lactam is 4-(4-chlorophenyl)-5-methylene-pyrrol-2-one.

10. The composition of claim 9, wherein the ratio of lactam to rhamnolipid is from 1:0.5 to 1:20.

11. The composition of claim 9 comprising 0.01 to 5% wt. lactam.

12. The composition of claim 9 comprising 0.01 to 2% wt. lactam.

13. The composition of claim 9, wherein the composition comprises 0.1% wt. to 4% wt rhamnolipid.

14. A composition comprising a solution comprising 4-(4-chlorophenyl)-5-methylene-pyrrol-2-one, 0.1% wt. to 4% wt glycolipid biosurfactant and water wherein the glycolipid biosurfactant is mono-rhamnolipid and/or di-rhamnolipid, and water.

15. The composition of claim 14, wherein the composition comprises 0.01 to 5% wt. 4-(4-chlorophenyl)-5-methylene-pyrrol-2-one.

16. A composition comprising a solution comprising 0.01 to 5% wt lactam and 20-90% wt mono-rhamnolipid and/or di-rhamnolipid, wherein the lactam is 4-(4-chlorophenyl)-5-methylene-pyrrol-2-one.

17. The composition of claim 16 comprising 20-90% wt di-rhamnolipid.

18. The composition of claim 16 comprising 20-90% wt mono-rhamnolipid and di-rhamnolipid.

* * * * *